United States Patent [19]

Aronson et al.

[11] Patent Number: 5,437,668
[45] Date of Patent: Aug. 1, 1995

[54] APPARATUS AND METHOD FOR CLINICAL USE OF LOAD MEASUREMENT IN DISTRACTION OSTEOGENESIS

[75] Inventors: James Aronson; John H. Harp, Jr., both of Little Rock, Ark.

[73] Assignee: Board of Trustees of the University of Ark., Little Rock, Ark.

[21] Appl. No.: 198,356

[22] Filed: Feb. 18, 1994

[51] Int. Cl.$^6$ ............................................. A61B 17/56
[52] U.S. Cl. ....................................... 606/57; 606/54; 606/56
[58] Field of Search .................................. 606/53-59; 128/898

[56] References Cited

U.S. PATENT DOCUMENTS

| | | | |
|---|---|---|---|
| 3,977,397 | 8/1976 | Kalnberz et al. | 606/54 |
| 4,127,119 | 11/1978 | Kronner | 606/56 |
| 4,312,336 | 1/1982 | Danieletto et al. | 606/57 |
| 4,615,338 | 10/1986 | Ilizarov et al. | |
| 5,087,258 | 2/1992 | Schewior | 606/56 |
| 5,108,394 | 4/1992 | Kurokawa et al. | |
| 5,180,380 | 1/1993 | Pursley et al. | |
| 5,275,598 | 1/1994 | Cook | 606/54 |

OTHER PUBLICATIONS

Younger, A. S. E.; "Forces Measured during Femoral Lengthening in Children; Simon Fraser University", Master's Thesis; Jun., 1990.
The Ilizarov External Fixator, Production Information, 1988.
The Ilizarov External Fixator, General Surgical Technique Brochure, 1988.
Viscoelastic Behavior of Tissue in Leg Lengthening by Distraction, Leong, et al., Mar.-Apr. 1979, Clinical Orthop.
Femoral Forces During Limb Lengthening in Children, Younger, et al., Feb. 8, 1997, British Columbia Children's Hospital, Vancouver.
Force and Stiffness Changes During Ilizarov Leg Lengthening, Wolfson, et al., Jan. 1990, Clinical Orthop.
In Vivo Measurement of Mechanical Forces Generated During During Distraction Osteogenesis, Aronson, et al., Mar. 4-7, 1991 Anaheim.
Data Acquistion System for Automatically Monitoring the Forces Applied During Bone Distraction in Canines, Halter Thesis, Dec. 1989, Univ. of Ark.

Primary Examiner—Peter A. Aschenbrenner
Attorney, Agent, or Firm—Ray F. Cox, Jr.

[57] ABSTRACT

Distraction Osteogenesis is a procedure for lengthening a bone. The Ilizarov External Fixator is an apparatus employed in the distraction osteogenesis procedure. The prospects for a successful clinical outcome of the procedure are enhanced by modifying the Ilizarov apparatus to obtain measurements of loads generated during the procedure. An apparatus and method for the clinical use of load measurements taken during the distraction osteogenesis procedure are disclosed. An alternative method is disclosed for converting load measurements to stress data in order to enhance the clinical outcome of the procedure. Additionally, the method may be employed to assess completion of the healing process.

6 Claims, 3 Drawing Sheets

APPARATUS AND METHOD FOR CLINICAL USE OF LOAD MEASUREMENT IN DISTRACTION OSTEOGENESIS

BACKGROUND OF THE INVENTION

The present invention relates to orthopedic instrumentation including external fixation devices and in particular to a method and apparatus for the clinical use of load measurements taken during distraction osteogenesis.

Distraction osteogenesis is a technique for lengthening a bone so as to minimize differences in the lengths of a patient's limbs or for similar purposes. Professor G. A. Ilizarov developed a technique for bone lengthening using the technique of distraction osteogenesis which employs an external fixator attached to the patient's bone by tensioned small diameter wires. The Ilizarov technique may be used for various orthopedic purposes other than bone distraction. A description of the Ilizarov technique may be found in U.S. Pat. No. 4,615,338 issued to Ilizarov, et al. on Oct. 7, 1986 for "Automatic Compression-Distraction Apparatus", incorporated herein by reference.

Typically the Ilizarov apparatus employs two or more fixator rings which may be either complete or partial rings. Transosseous wires and/or pins are fixed to the fixator rings at each of their ends by means of wire fixation bolts after being passed through holes drilled in the patient's bone and through the soft tissue of the limb. In the basic form of the Ilizarov apparatus, distraction rod assemblies are attached to the fixator rings. The distraction rod assemblies comprise threaded rods and telescopic rods into which the threaded rods are received. The distraction rod assemblies may be fastened to the fixator rings using nuts or knobs which may be turned to gradually lengthen the distraction rod assemblies so as to force the fixator rings further apart.

For distraction osteogenesis of a leg bone the Ilizarov apparatus is used in the following manner. A site is selected on the bone to be lengthened. The external fixator rings are attached to the patient's leg on either side of the selected site by means of the transosseous wires which are passed through the soft tissue and bone of the patient's limb. The transosseous wires are attached at their opposite ends to the respective fixator rings. A corticotomy is performed through a small incision in the patient's limb. The patient's bone is separated at the selected site while preserving the blood supply within the interior of the bone and with minimal damage to the soft tissue in the vicinity of the severed bone. Following surgery, nuts on the distraction rods may be tightened to force the fixator rings apart and thereby applying tension to the tissues in the biological zone between the bony surfaces at the corticotomy site. Bony regeneration at the surface of the severed bone begins to occur as the process of distraction continues. The typical rate of distraction is approximately 1 mm per day until the necessary length of regenerated bone is achieved. Afterwards the external fixator is kept in place until the newly generated bone has stabilized.

While distraction osteogenesis is typically performed by manual adjustment of the rate of distraction, systems have been suggested for automatic distraction. U.S. Pat. No. 5,180,380 issued to Pursley, et al. on Jan. 19, 1993 for "Automatic Compression-Distraction-Torsion Method and Apparatus" discloses a system which includes at least one motor for incrementally adjusting the distraction rods.

U.S. Pat. No. 5,108,394 issued to Kurokawa, et al. on Apr. 28, 1992 for "Bone Fixing Device" discloses a bone fixing device comprising a single rod member and an axial actuator. Kurokawa furthermore discloses a load cell for detecting what is described as a repulsive force from the bone.

Various attempts have been made to understand the biomechanical forces involved in the distraction osteogenesis procedure. However, the studies to date have simply focused on the nature of the loads generated during the distraction process without attempting to apply that information in a clinical setting to improve the clinical outcome. Prior to the development of the method and apparatus of the present invention, distraction has been carried out at a fixed rate regardless of the loads generated in the patient during the process. It has been discovered that a knowledge of the loads generated by the distraction procedure across the active biological zone of the corticotomy site may be used to adjust the rate of distraction to avoid unsuccessful clinical outcomes. An unsuccessful clinical outcome could include either premature consolidation of the biological bridge between the surfaces of the severed bone or nonunion which is a result of a disruption of the biological bridge. In addition, the information derived from the measurement of loads at the corticotomy site may be used to test the degree of bony consolidation at the corticotomy site and thus to determine when healing has progressed to the point that the fixator may be removed from the patient.

Furthermore, prior to the development of the method and apparatus of the present invention, no consideration has been given to the variation in cross-sectional area of the bone in various patients. As a result there has been no recognition of the variation in stress or load per unit area in various patients in which the loads alone would appear to be otherwise similar. The method and apparatus of the present invention recognizes that an improved clinical outcome may be obtained by converting measured load information into stress values by comparing the measured loads to the measured cross-sectional area of the corticotomy site. The use of such derived stress information may then be applied to adjust the rate of distraction so as to avoid unsuccessful clinical outcomes.

Other objects, advantages and features of the present invention will be more fully understood when considered in conjunction with the following detailed description of the preferred embodiments together with the drawings.

DETAILED DESCRIPTION OF THE PREFERRED EMBODIMENTS

Limb lengthening requires the stretching of soft tissues such as muscle, fascia and skin. Distraction osteogenesis necessarily creates a biological interface between the cut bone surfaces which adds further resistance to the stretching. The mechanical environment for distraction osteogenesis seems to play an important role in successful bone formation and bridging.

External fixators provide a convenient vehicle to monitor the reactive forces during limb lengthening. These forces may indicate pathological conditions that would allow one to alter the treatment regimen such as the rate of stretching in order to avoid clinical damage.

Bone lengthening using the technique of distraction osteogenesis depends upon: preservation of the blood supply to each bony surface by a low-energy corticotomy, slow and gradual distraction of the resultant biological bridge and stable fixation to avoid complete disruption of the microstructures within the osteogenic zone. As the generator of distraction osteogenesis, the fixator must be able to withstand superimposed forces from sources such as soft tissue resistance to stretching or loads from weightbearing.

The Ilizarov external fixator commonly used in bone lengthening procedures is mechanically unique compared to other external fixators. With circumferential load cells, the circular external fixator can directly measure the axial load during lengthening.

PUBLISHED STUDIES

There are several published studies concerning loads generated during limb lengthening procedures. White and Kenwright ("The Timing of Distraction of an Osteotomy," *J. Bone Joint Surg.*, 1990) measured rabbit tibia distraction forces in a uniplanar bilateral external fixator during a 10% lengthening that utilized a diaphyseal osteotomy. The maximum load was 45 Newtons when distraction was started immediately after surgery and 95 Newtons when delayed for seven days. Leong and his coworkers were the first to measure distraction loads in-vivo during a human limb lengthening procedure using a bilateral external fixator. ("Viscoelastic Behavior of Tissue in Leg Lengthening by Distraction, "*Clin Orthop.*, 1979) Distraction loads were measured in three patients undergoing tibial lengthenings of 38 mm, 37 mm and 39 mm; the maximum measured loads in these cases were 236 Newtons, 163 Newtons, and 183 Newtons respectively. Wolfson measured in-vivo distraction loads in the tibia of an 11-year old female patient undergoing 30 mm lengthening using the Ilizarov method with a metaphyseal corticotomy distracted 0.25 mm four times daily for fifty days. ("Force and Stiffness Changes during Ilizarov Leg Lengthening," *Clin. Orthop.*, 1990). The maximum load was 245 Newtons at forty-four days after surgery. The axial stiffness of the distracted limb was reported to increase throughout the procedure and this was attributed to either soft tissue viscoelasticity or mineralization of the distraction gap tissue. Verkerke instrumented a Wagner fixator used for femoral lengthenings in two patients. ("Design of a Load Cell for the Wagner Distractor," *Proc. Instn. Mech Engrs, Part H: Journal of Engineering in Medicine*, 1989). The maximum loads measured were 270 Newtons after a 60 mm lengthening, and 400 Newtons after a 28 mm lengthening.

Steen studied forces and bone motions during lengthening of the ovine tibia and compared diaphyseal and metaphyseal osteotomy sites. ("Biomechanical Factors in the Metaphyseal- and Diaphyseal-Lengthening Osteotomy: An Experimental and Theoretic Analysis in the Ovine Tibia," *Clin Orthop.*, 1990) Loads were estimated indirectly from computed tomography scans and load factors derived from electromyographic studies. The calculated compression load was estimated to be 210% higher at the metaphyseal osteotomy compared to the diaphyseal site. A numerical model was also used and it predicted a residual passive tissue tension of 431 Newtons after a lengthening of 26 mm.

METHOD OF DISTRACTION OSTEOGENESIS

Figure 1:
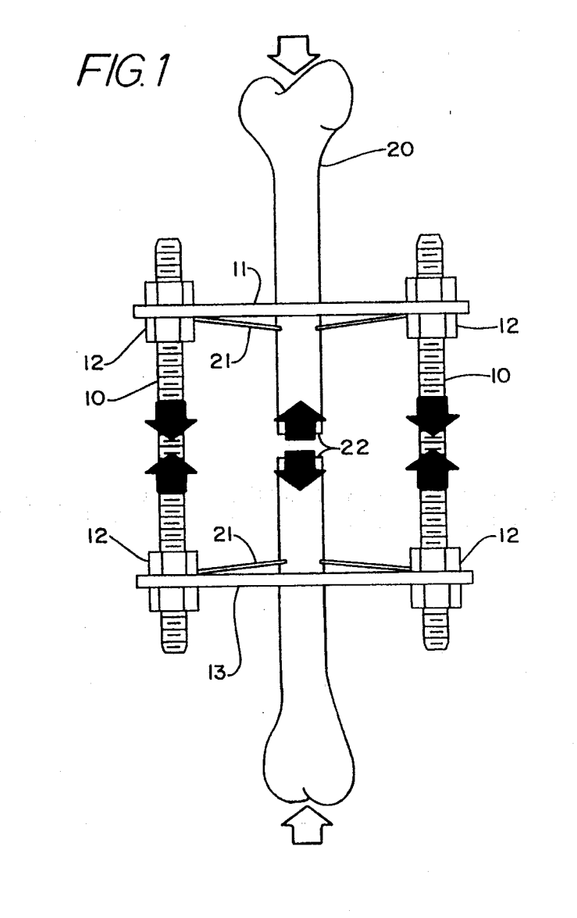
FIG. 1 is a plan view of an external fixator showing the loads generated during distraction.
Figure 2:
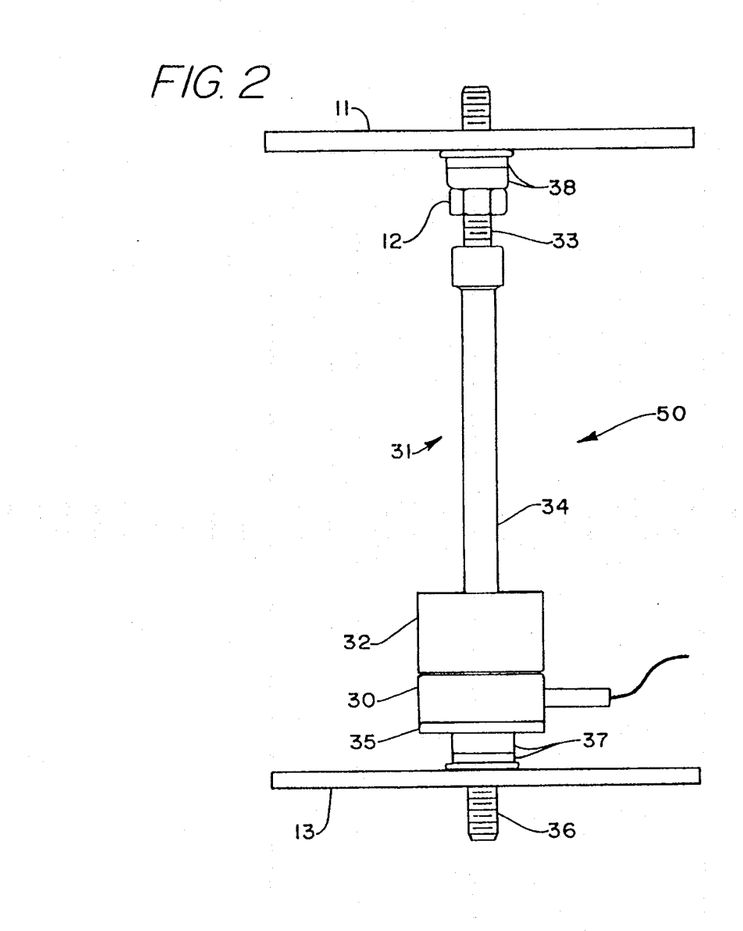
FIG. 2 is an elevation view of the distraction rod assembly of the present invention.
Figure 3:
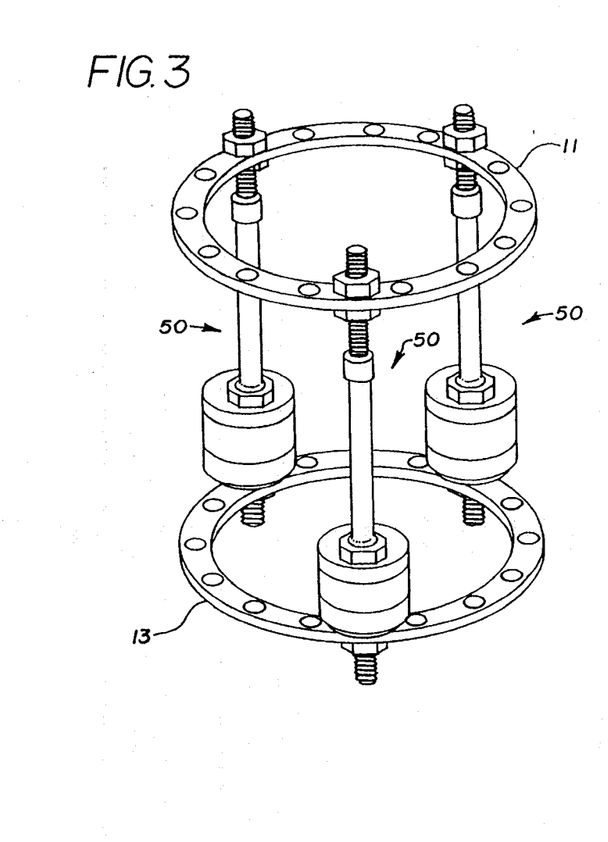
FIG. 3 is a perspective view of an external fixator employing the load measurement distraction rods of the present invention.
Figure 4:
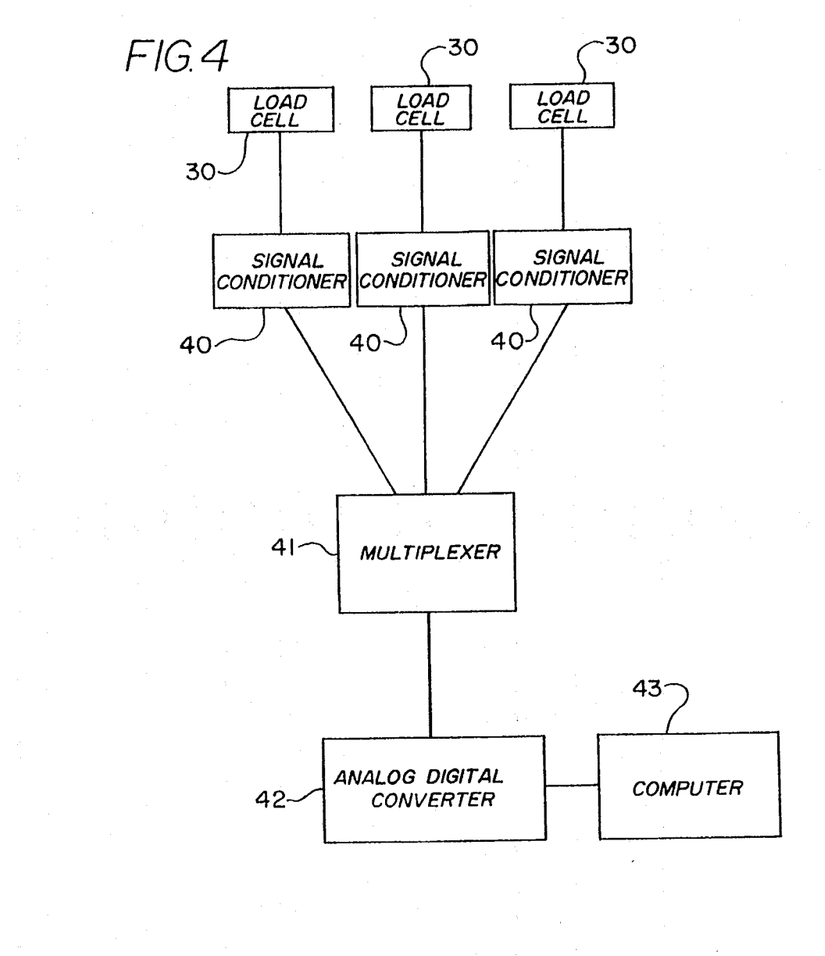
FIG. 4 is a schematic of the data processing apparatus associated with the present invention.

Although the above studies involve different fixators, bones and distraction techniques, they are based on the same general biomechanical principle shown in FIG. 1. A bone 20 has been severed by a corticotomy or similar procedure. On either side of the corticotomy site 22 transosseous wires 21 have been inserted through the bone 20 and affixed to upper and lower fixator rings 11, 13 respectively. The fixator rings 11, 13 are held apart by threaded rods 10 which are threaded to receive nuts 12. The nuts 12 may be employed to force the fixator rings 11 apart. The result is an applied axial tension in the bone 20 and corresponding compressive forces in the threaded rods 10. The sum of the axial compressive loads in the threaded rods 10 is equal to the total tissue tension in the limb. A large percentage of the distraction load is generated by the tissue in the osteogenic zone. Therefore the distraction load may also provide indirect information about the biological status of the tissue under distraction. The apparatus of FIG. 1 is a generalized version of the prior art which is modified in the present invention as shown in FIGS. 2–4.

Loads measured from external fixators have been used to guide clinical decisions during fracture healing. Leong proposed that the forces created during limb lengthening relate directly to distraction rate and length. Verkerke theorized that forces created by limb lengthening are due to resistance in distracted soft tissues and soft tissue injury might be avoided by limiting force generation. In a series of patients undergoing limb lengthening, Kenwright attempted to avoid physeal fracture by using measured fixator loads to control distraction.

THE APPARATUS OF THE PRESENT INVENTION

The present invention is based on the discovery that a relationship exists between distraction load or stress and clinical outcome; i.e., union versus non-union or premature consolidation.

In order to determine distraction loads for the purposes of the present invention, an instrumentation system was developed that could measure distraction loads in an Ilizarov fixator. The system was used experimentally to measure loads in canine subjects undergoing tibial lengthening. The clinical outcome of the lengthening was determined from radiographs and the load data was examined for prognostic value.

The strain gauge based instrumentation system was developed to meet several design criteria. Loads were measured in the distraction rods since the sum of the rod compressive forces would equal the total tensile force in the distracted limb. Eccentric loads that would cause bending moments in the distraction rods and inaccurate load readings had to be eliminated by moment-free connections. The load measuring apparatus had to be small enough to clear the soft tissues when mounted on the fixator.

In order to use commercially available transducers, hardware was designed to allow the transducers to be fitted to the Ilizarov fixator.

The load cell distraction assembly 50 is described with reference to FIG. 2. To allow the incorporation of load cells 30, mounts 32, 35 are designed to affix to telescopic distraction rod assemblies 31. The telescopic distraction rod assemblies 31, which replace the simple threaded rod 10 of FIG. 1, comprise a threaded distraction rod 33 threadedly received in a telescoping rod 34. A separate alignment rod 36 is attached to the lower fixator ring 13 and is employed to facilitate assembly of the load cell 30, the lower mount 35 and the lower coupled hemispherical washers 37. The mounts 32, 35 are designed to insure axial loading of the load cells 30 during distraction. The mounts 32, 35 are made of 440C stainless steel and therefore may be used in a sterile environment. The load cells 30 require hardened mating surfaces, so the mounts 32, 35 are heat treated to a hardness of 60 Rockwell C. An upper mount 32 is rigidly affixed to the telescoping rod 34. A lower mount 35 is assembled to the distraction rod assemblies 31 as will be described more fully below.

A prefabricated load cell 30 is used that not only meets the above design criteria but also fits over the alignment rod 36 with minor modifications. The 900 Newton capacity cannulated load cell 33 is mounted in hardened steel mounts 32, 35. The load cell 30 has a hollow annulus which permits the alignment rod 36 to be passed through it.

It has been found that a suitable load cell 30 is the AL Design, Inc. Model ALD-W-5 compact, temperature compensated load transducer designed to approximate the configuration of regular bolt washers. Each load cell 30 has a full Wheatstone Bridge circuit with the strain sensitive elements attached to a load column resulting in a linear output signal which is a function of load. Each load cell 30 has a capacity of 200 pounds force (890 Newtons) and a nominal sensitivity of 2.0 millivolts per volt of excitation at 200 pounds force. Since the actual sensitivity of each load cell 30 is slightly different from the nominal value, each is matched to a signal conditioner 40 with the appropriate gain to produce 5 volts DC output at full load as will be described more fully below.

The load cell 30 is seated between mounts 32, 35 in line with the distraction rod 33 and alignment rod 36. The mounts 32, 35 are then connected to upper and lower coupled hemispherical washers 37, 38 (conical washers, Smith and Nephew Richards, Memphis, Tenn.) to eliminate bending loads. The pure axial load is transmitted from the upper fixator ring 11 to upper hemispherical washers 38 to the distraction rod 33 and telescoping rod 34, through the upper mount 32 to the load cell 30 across the lower mount 35 to the lower hemispherical washers 37 and finally into the lower fixator ring 13.

The load measuring system for each external fixator consists of three identical load cell distraction assemblies 50 as shown in FIG. 3. Referring to FIG. 4, the load cell 30 in each load cell distraction assembly 50 is driven by a transducer signal conditioner 40 modified for a zeroing offset adjustment. A suitable device is Analog Devices Model 1B32AN Bridge Transducer Signal Conditioner. These devices offer programmable gain and excitation, a common mode rejection ratio of 150 dB (60 Hz G=1000), remote sensing of excitation, and a 4 Hz, 3-pole low pass filter with a 60 dB per decade roll off. The filter reduces line noise and improves the signal to noise ratio. Because the forces within the system are slowly varying, the narrow bandwidth of the 1B32AN poses no problems. Since the mounting card for the 1B32AN does not offer outboarding of the offset adjustments (zero suppression) for the amplifier, the mounting cards may be modified to allow offset adjustments to be made from the front panel of the instrument.

Because of the difference in sensitivity of each load cell 30, each should be matched to a signal conditioner 40. The gain of each signal conditioner 40 is set to produce a signal ranging from 0 to 5 volts for a full scale measurand (890 and 2224 Newtons force). The signals are multiplexed to a high speed analog to digital converter (ADC) 42 through a multiplexer 41.

In order to record the output of all the load cells 30 in a reasonable period of time and to make data collection less rigorous, the outputs of the load cell 30, after conditioning, are connected via a 16 channel multiplexer 41 to a high speed ADC 42 operating in one of the I/O slots of an IBM compatible computer 43. An acceptable 12-bit ADC 42 is a Daisi Model DAI-120 Data Acquisition Module. The DAI-120 has a 50 k-Hz sampling rate, 125 ns aperture time and a 12 $\mu$s settling time. This module allows for any of 16 analog input signals to be independently selected by the user.

SOFTWARE

The software developed for this system is a menu driven, interactive program developed specifically for the present invention. The software consists of several menus which guide the user through the testing procedure. Error trapping is incorporated to check the validity of the user's response. As an aid in record keeping, each data file is tagged with a header file which contains information about the test. The user is prompted to answer a group of questions pertaining to the test with a default value listed with each question. These header files are also used to acquire the information needed to gather data and are stored as a random access data files. Since the values returned from the analog to digital converter 42 are proportional to the output of the load cells 30, these values must be converted to values that are dimensionally the same as the measurand. This conversion is performed prior to the data being stored or displayed. Forces are given in Newtons and the displacements in millimeters. Since the monitored parameters within the system fluctuate slowly and each test may exceed two hours in length, a data accumulation rate of one sample every ten seconds is selected. This permits an adequate number of samples to be accumulated allowing representative plots of the data to be generated.

To assist in setting up the test equipment, real-time signal output from the load cells 30 may be displayed on the computer monitor. This allows offset voltages to be removed from the system prior to data accumulation. Output signals from the load cells 30 are also continuously displayed while data is being accumulated.

After creating the header file the user is directed to the data acquisition section of the program. In this section the user is first allowed to zero the system, and then asked to input the length of time over which data is to be accumulated. At this point, control is passed to the computer. The ADC channels which the user selected when setting up the header file are read and the data stored and displayed for the desired time interval. At any time data acquisition may be halted without loss of data. The data is stored to an array and then written to a disk file.

Other options provided within the software are subroutines for printing out data and header files, plotting data on the screen and dumping screens to the printer. These options have a convenient means of evaluating the data.

LOAD CELL ASSEMBLY TESTING

The washer type load cell 30 is designed around strain gauges bonded to a central aluminum ring. Load is transmitted to the ring element by mechanical bearing on this thin edge which is 0.35 mm thick and 10.8 mm in outside diameter. This mechanical connection is exquisitely sensitive to slight flatness imperfections in the bearing surfaces. To eliminate variability in readings due to this characteristic, the assemblies 50 are tested individually with dead weights to determine the optimal alignment of the hemispherical washers 37, 38, load cell 30 and mounts 32, 35. This alignment is then used in all further testing.

The assemblies 50 were tested in a testing jig to model an Ilizarov type configuration. A 120 mm diameter Ilizarov ring (Part Number 101202, Richards Smith Nephew, Memphis) was connected with three load cell distraction assemblies 50 to a 12 mm aluminum plate drilled to match the ring pattern. A single fixed rod was bolted to the plate and passed through the upper ring to provide mechanical stability. An aluminum platen bolted to a 25 mm aluminum rod was connected to the proximal ring with tensioned 1.8 mm smooth wires (Part Number 102100, Richards Smith Nephew, Memphis). Loads were applied to the platen with an Instron testing machine. Load magnitude and location were varied to stimulate different axial loads and bending moments. The system error was found to be less than 10% of the applied load.

EXAMPLE PROCEDURE

A group of mature hounds undergoing tibial lengthening by the Ilizarov technique were used for a source of load readings. This group consisted of twenty-one dogs with either metaphyseal or diaphyseal corticotomies and varying latency periods between surgery and the start of distraction. The Ilizarov external fixator had been surgically applied with a 260° upper ring 11 and a full lower ring 13. Two 1.8 mm transosseous wires 21 were tensioned and bolted to each ring 11, 13. Three distraction rods 10 were evenly distributed between the rings 11, 13. All subjects were distracted a total of 28 mm (about 15% increase over baseline) at the rate of one mm/day by two 0.5 mm distractions in the morning and evening.

At one week intervals during the four week distraction phase the subjects were sedated and positioned supine on a holding frame. The external fixator was suspended so the tibia was horizontal to eliminate gravity loads. A dial caliper (Mitutoyo #505-635-50, Japan) was used to measure the baseline ring separation at the three distraction rod 10 locations. The load cell distraction assemblies 50 were installed and the load transferred from the distraction rods 10 to the load cell distraction assembly 50 by loosening the nuts 12 on the distraction rods 10 which were left loosely in place to provide translational control between the rings 11, 13. Load measurements were recorded for one minute before distracting each rod 0.5 mm. Loads were then measured for an additional nine minutes. After the monitoring period the load cell distraction assemblies 50 were removed and the rings 11, 13 reset to the proper position.

It is typical of distraction osteogenesis that loads show an instantaneous increase upon distraction followed by a gradual decline in load as stressed tissues relax. There is also an overall general increase in load over time as limb lengthening progresses. Once distraction is completed and bony consolidation begins, loads measured in the distraction apparatus decrease as more of the load is borne by the increasingly stiff bony tissue of the limb.

Each subject was studied with a Siemens Somaton DR3 CT scanner prior to surgery and at the end of distraction. A scout view and serial 4 mm axial slices along the tibia were obtained. The baseline tibia length was measured from the scout view. The cross-sectional area of the osteogenic zone at the end of distraction was computed at the scanner console by outlining a freehand region of interest around the new bone. The axial images were later processed to obtain the area of soft tissue at the osteogenic zone using a video image processing computer program (Image Analyst, Automatix, Billeerica, Mass.) running on a Macintosh IIx system.

Plain radiographs in the A-P and lateral projections were obtained at weekly intervals during distraction, at fixator removal, and prior to sacrifice. An aluminum stepwedge was used for density control.

The radiographs were examined during the distraction phase for signs of premature fusion of the osteogenic zone. These signs included radiodense bridging of the corticotomy site 22 and excessive deflection of the transosseous pins 21. The clinical outcome of the lengthening procedure was determined from examination of the last radiograph prior to sacrifice. Observer bias was prevented by using an investigator to analyze the radiographs who was unaware of the load measurement results. An outcome was judged to be a nonunion if there was a continuous radiolucency in the osteogenic area. An outcome of malunion was assigned if angular deformity (>5 degrees) existed without signs of a nonunion.

The variables for each subject were baseline tibia length, osteogenic zone area, soft tissue area at the osteogenic zone, latency from surgery to start of distraction, and distraction loads at weekly intervals. This data was grouped by both osteotomy site and outcome then analyzed using the BMDP statistics package (BMDP Statistical Software, Inc., Los Angeles, Calif. 90025). The BMDP programs used were 3D (T - Tests), 1R (Linear Regression by Groups), and 5V (Unbalanced Repeated Measures Models with Structured Covariance Matrices).

Six dogs had premature fusions early during the distraction phase. These were easily discernable on the plain radiographs. Loads were measured in these subjects within the safety limits of the load cells 30 so as not to overload the gauges and endanger the instrumentation system.

Fifteen dogs completed the distraction load measurement phase of the study. One animal died of lymphosarcoma (unrelated to the experimental protocol) prior to scheduled sacrifice. Fourteen dogs completed the entire protocol to final bone healing for outcome assessment. The clinical outcomes of these fourteen dogs were assessed radiographically prior to sacrifice at day 119 after surgery. There were eleven unions and three nonunions at the completion of the study. Two of the unions developed angular deformity that was felt to be secondary to premature removal of the fixator. These results are summarized in Table 1.

TABLE 1

| | | Subject Groupings and Outcomes | | | |
|---|---|---|---|---|---|
| | | | Outcome | | |
| Corticotomy Site | Latency (Days) | Non-union | Union with Deformity | Normal Union | Premature Fusion |
| Metaphyseal | 0 | | | 2 | |
| | 7 | | 1 | 1 | |
| | 14 | | | | 2 |
| | 21 | | | | 3 |
| Diaphyseal | 0 | | | 3 | |
| | 7 | 1 | | 1 | |
| | 14 | 1 | 1 | 1 | |
| | 21 | 1 | | 1 | 1 |

No significant difference was found by t-test in the baseline tibia length when grouped by corticotomy site ($p=0.6424$). There was a significant difference between osteogenic cross-sectional areas ($p=0.0138$) as calculated by CT scans; the mean (and standard deviation) of the metaphyseal sites were 3.31 cm$^2$(0.57) and of the diaphyseal sites were 2.34 cm$^2$(0.43).

Figure 5A:
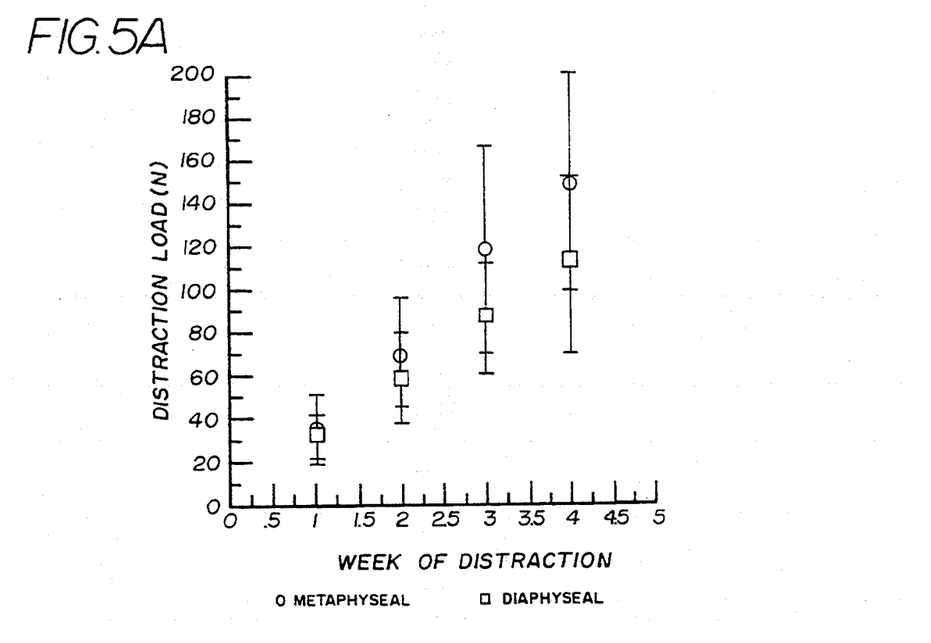
FIG. 5A is a graph of distraction loads versus week of distraction for metaphyseal versus diaphyseal sites.

The mean (and standard deviation) of the weekly load measurements are shown in FIG. 5A grouped by corticotomy site. Diaphyseal (n=40) and metaphyseal (n=20) observations from 15 subjects were divided evenly over the four observation periods. The mean load at the end of distraction was 155 Newtons for metaphyseal (n=5) and 111 Newtons for the diaphyseal (n=10) sites respectively.

Load based on the time from surgery was highly significant ($p<0.0001$). The effect of corticotomy site was also significant ($p=0.0207$). The interaction of time and corticotomy site was suggestive, but not quite significant ($p=0.056$).

A linear regression by groups was performed on the distraction loads vs. time and is shown in Table 2. For all data as a single group, $R^2=0.55$ ($p<0.0001$). An analysis of variance of regression coefficients over groups was highly significant ($p=0.00161$) indicating the slopes of the regression lines between metaphyseal and diaphyseal sites are statistically different for measured loads over time. The individual distraction loads were then divided by the respective cross-sectional area of the osteogenic zone in each subject. The resulting quantity was called the "osteogenic zone stress"; the regression analysis on this data is also in Table 2. For all data as a single group, $R^2=0.50$ ($p<0.0001$). An analysis of variance of regression coefficients over groups was not significant ($p=0.87$) indicating there was no statistical difference in the slopes of the regression lines for calculated stress.

This procedure was repeated using the cross-sectional area of all soft tissue in the osteogenic zone to calculate the "soft tissue stress". $R^2=0.42$ ($p<0.0001$) for all data as a group, and analysis of variance of the regression coefficients between groups was still significant ($p=0.0005$).

Figure 5B:
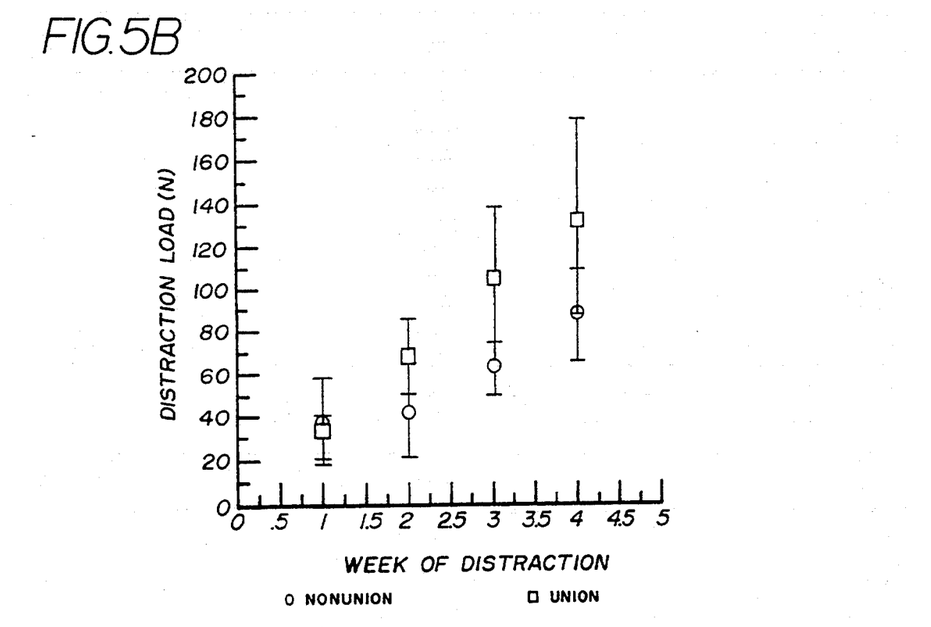
FIG. 5B is a graph illustrating clinical outcome in terms of distraction load.

There was a significant difference in the baseline tibia length ($p=0.0292$) when grouped by outcome. The mean lengths and standard deviations were 175 mm (5.24) and 185 mm (9.70) for the unions and nonunions respectively. Furthermore, the three nonunions had osteotomies at the diaphyseal site. There were no significant differences in latency, osteogenic zone area, or soft tissue area. A linear regression of the load readings demonstrated a significant difference in the slopes ($p<0.023$) as shown in Table 2. The mean (and standard deviation) of the weekly load measurements are shown in FIG. 5B grouped by outcome. When compared by t-test there was a significant difference in loads at the end of the third week ($p=0.044$). There was a suggestive change at the end of the second week ($p=0.056$). No significant difference was found in the other weekly measurements.

TABLE 2

| Linear Regression Statistical Analysis | | | | | | |
|---|---|---|---|---|---|---|
| Calculation Method | Group | $R^2$ | $p<$ | Slope | Intercept | p, difference in regression lines |
| Loads Only | Metaphyseal | 0.65 | 0.0001 | 5.69 | −1.19 | 0.0016 |
| | Diaphyseal | 0.58 | 0.0001 | 3.80 | 5.43 | |
| Loads/Osteogenic Zone Area | Metaphyseal | 0.61 | 0.0001 | 1.78 | −1.06 | 0.8731 |
| | Diaphyseal | 0.46 | 0.0001 | 1.74 | 1.78 | |
| Loads/Soft Tissue Area | Metaphyseal | 0.62 | 0.0001 | 0.18 | −0.10 | 0.0005 |
| | Diaphyseal | 0.48 | 0.0001 | 0.28 | 0.45 | |
| Loads Only | Nonunion | 0.56 | 0.0047 | 2.42 | 13.96 | 0.0028 |
| | Normal Union | 0.63 | 0.0001 | 4.79 | −0.15 | |

This study shows that distraction loads increase with time during the actual lengthening. No appreciable decay in load was seen between the weekly measurements. Empirically, elastic tissue resistance is the most likely cause of the force increase.

This study statistically supports earlier case reports that suggest distraction loads vary with corticotomy site (metaphyseal vs. diaphyseal). We hypothesized that this load is directly related to distraction of the collagenous bridge central to the osteogenic interzone. This was supported statistically when the measured loads were converted to stress by dividing the osteogenic zone area into the load. When metaphyseal stresses were compared to diaphyseal stresses by linear regression, there was no longer a significant difference between groups and the regression lines for the two groups were essentially parallel and collinear. When the loads were normalized by the soft tissue area, a significant difference between the metaphyseal and diaphyseal groups remained, consistent with the hypothesis that a large portion of the distraction load is generated in the fibrous interzone.

This study suggests that distraction loads measured during the actual limb lengthening are useful in predicting the clinical outcome of the procedure. The nonunion group (n=3) had statistically significant lower loads at the end of week three than the normal group (n=11).

The significant difference in tibia length between outcome groups could be due to chance since multiple statistical comparisons were performed on a small group of subjects. If nonunions are less resistant to distraction (lower loads), these tibiae would stretch further for a given fixator distraction, which could account for the increased tibial length, a mean of 10 mm at the end of distraction. Low load measurements during the distraction phase may indicate low axial stiffness which may lead to mechanical instability and larger movements in the osteogenic zone. Larger distraction increments or macromotion could disrupt normal tissue differentiation and result in a nonunion. Alternatively, inadequate collagenous bridging may be less resistant to distraction loads. Nonunions stem from fibrocartilage and necrotic, loose connective tissue, both of which contain less collagen and are therefore less stiff and result in lower loads early in the distraction phase. A high early load in the distraction phase is a sign of premature consolidation. Normal load increments indicate appropriate collagen bridging across the fibrous interzone.

SUMMARY OF EXAMPLE PROCEDURE

Direct axial loads were measured weekly during a 15% left tibial lengthening in 21 skeletally mature dogs using three in-line load cells mounted between the rings of an Ilizarov external fixator. The loads all increased linearly over time to a maximum at the end of distraction (week 4). The metaphyseal lengthening site (mean 155 Newtons) generated significantly higher loads than diaphyseal sites (mean 111 Newtons). Stress was calculated by dividing measured load by the CT measured cross-sectional area of each distraction osteogenesis site; the metaphyseal and diaphyseal groups demonstrated equal stress at each time point with a maximum of 47 Newtons/cm$^2$ at the end of distraction. Six premature consolidations occurred that demonstrated loads significantly greater than 200 Newtons by week 2 of distraction. Three nonunions occurred which had significantly lower loads measured by week 3 of distraction (mean 60 Newtons or 26 Newtons/cm$^2$). It is well known in the art that, with adjustments for the greater cross-sectional area of human bones, experimental data on canines is directly transferable to human patients.

CONCLUSION

The apparatus of the present invention may be used to measure moment free axial loads in the bones of patients undergoing the distraction osteogenesis procedure using an Ilizarov external fixator. By measuring actual loads generated during the distraction procedure, the method of the present invention may be employed to improve the clinical outcome of the procedure. By avoiding loads on the biological zone of the corticotomy site that are neither too high nor too low, it is possible to avoid nonunion or premature consolidations. For human patients a load range from approximately 20 Newtons early in distraction to approximately 500 Newtons late in distraction is desirable.

Furthermore, the effectiveness of the method of the present invention may be improved by employing a variation on the method in which measurements of the cross sectional area of the corticotomy site may be used to calculate the stress at the corticotomy site rather than the total load at the corticotomy site. It is therefore possible to effect a normalization which reflects the variation in the cross sectional area of the corticotomy site in various patients. A stress range from approximately 27 Newtons per square centimeter to approximately 100 Newtons per square centimeter is desirable while a stress range from approximately 45 Newtons per square centimeter to approximately 50 Newtons per square centimeter appears to be optimal by approximately three weeks of distraction.

Further, the apparatus and method of the present invention may be employed in the end stages of the distraction procedure to assess the end of healing. After the desired degree of limb lengthening is achieved, the corticotomy site will not have completed bony consolidation. The degree of bony consolidation is assessed by loading the patient's limb; for example, by having the patient stand on the leg on which the distraction has been performed. Loads are measured across the corticotomy site. As the degree of bony consolidation progresses, the consolidated bony tissue is able to carry proportionally more of the load on the limb. When essentially all of the load is carried by the limb and not by the fixator, bony consolidation, and therefor healing, is complete and the fixator may be removed.

Although the apparatus and method of the present invention are described with respect to certain preferred embodiments, one skilled in the art would recognize that other variations are possible without departing from the scope of the invention as set forth in the appended claims.

What is claimed is:

1. A method for the clinical use of load measurements taken during distraction osteogenesis in which an external fixator having moment-free distraction means coupled to cannulated load cells is employed to distract a corticotomy site, comprising the steps of:
   (a) performing a corticotomy at a selected corticotomy site;
   (b) surgically affixing an external fixator having upper and lower fixator rings across said corticotomy site employing transosseous wires;
   (c) coupling, to distractor rod assemblies, canulated load cells producing analog electrical signals proportional to a load impressed on said load cells;
   (d) using moment-free connections, attaching at least three distraction rod assemblies to said upper and lower fixator rings;
   (e) periodically distracting said corticotomy site;
   (f) processing said electrical signals to derive said load across said corticotomy site;
   (g) adjusting the rate of distraction of said corticotomy site to maintain said load across said corticotomy site within a load range sufficiently high to avoid premature consolidation of said corticotomy site and sufficiently low to avoid nonunion of said corticotomy site.

2. The method of claim 1 wherein said load range is from approximately 20 Newtons early in distraction to approximately 500 Newtons late in distraction.

3. The method of claim 1 comprising the additional steps of measuring the cross-sectional area of said corticotomy site, calculating the stress across said corticotomy site, and adjusting the rate of distraction of said corticotomy site to maintain said stress across said corticotomy site within a stress range sufficiently high to avoid premature consolidation of said corticotomy site and sufficiently low to avoid nonunion of said corticotomy site.

4. The method of claim 3 wherein said stress range is from approximately 27 Newtons per square centimeter to approximately 100 Newtons per square centimeter.

5. The method of claim 3 wherein said stress range is from approximately 45 Newtons per square centimeter to approximately 50 Newtons per square centimeter by approximately week three of distraction.

6. The method of claim 1, comprising the additional steps of:
(a) after the required amount of limb lengthening is achieved, periodically placing an external load on the corticotomy site;
(b) measuring the load across the corticotomy site to test for bony consolidation; and
(c) removing the external fixator when the degree of bony consolidation indicates completion of healing.

* * * * *